United States Patent [19]
Lume-Pereira

[11] Patent Number: 5,914,432
[45] Date of Patent: Jun. 22, 1999

[54] HYDROGENATION OF HALOGENATED COMPOUNDS

[75] Inventor: Celio Lume-Pereira, Stade, Germany

[73] Assignee: The Dow Chemical Company, Midland, Mich.

[21] Appl. No.: 08/809,742

[22] PCT Filed: Nov. 15, 1995

[86] PCT No.: PCT/US95/14876

§ 371 Date: Mar. 27, 1997

§ 102(e) Date: Mar. 27, 1997

[87] PCT Pub. No.: WO96/16922

PCT Pub. Date: Jun. 6, 1996

[30] Foreign Application Priority Data

Nov. 28, 1994 [EP] European Pat. Off. ............. 94810671

[51] Int. Cl.$^6$ ............................ C07C 17/38; C07C 19/08
[52] U.S. Cl. ...................... 570/262; 570/181; 570/261; 570/175; 570/101; 570/177
[58] Field of Search .................... 570/261, 267, 570/181, 101, 177, 175

[56] References Cited

U.S. PATENT DOCUMENTS

| | | | |
|---|---|---|---|
| 2,118,662 | 5/1938 | Baumann et al. | 570/101 |
| 4,145,367 | 3/1979 | Boozalis et al. | 570/262 |
| 4,899,001 | 2/1990 | Kalnes et al. | 585/310 |
| 5,013,424 | 5/1991 | James, Jr. et al. | 208/78 |
| 5,068,484 | 11/1991 | James, Jr. et al. | 585/469 |
| 5,314,614 | 5/1994 | Moser et al. | 208/262.1 |
| 5,316,663 | 5/1994 | James, Jr. | 208/262.1 |
| 5,780,695 | 7/1998 | Kalnes | 570/262 |

FOREIGN PATENT DOCUMENTS

| | | |
|---|---|---|
| A10 028 824 | 5/1981 | European Pat. Off. . |
| 0 541 871 | 5/1993 | European Pat. Off. . |
| A10 682 100 | 11/1995 | European Pat. Off. . |
| 839756 | 6/1960 | United Kingdom . |
| 1008175 | 10/1965 | United Kingdom . |
| 2108953 | 5/1983 | United Kingdom . |
| WO 94/07825 | 4/1994 | WIPO . |

OTHER PUBLICATIONS

Abstract of CA 116:255051, 1992.
Abstract of CA 88:169335, 1978.
Abstract of CA 85:176349, 1976.
Chemical Abstracts 116:255051; Studies on Hydrogenation with Nickel Catalysts; Sakai et al; 1992.
Chemical Abstracts 85:176349; Active Palladium Catalyst for Hydrogenation of Organic Compounds; Teleshev et al, 1976.
Chemical Abstracts 88:169335; Study of Hydrogenation of Olefins Catalyzed by Polymer–Bound Palladium (II) Complexes; Terasawa et al, 1978.

*Primary Examiner*—John Kight
*Assistant Examiner*—D. Margaret M. Mach

[57] ABSTRACT

A halogenated compound (I) containing one or more >C=O, olefinic and/or aromatic >C=C< groups is hydrogenated for producing a halogenated compound (II) having no or a decreased level of >C=O, olefinic and/or aromatic >C=C< groups. In the hydrogenation process a liquid feed stream comprising one or more of these compounds (I) is contacted with a hydrogen-rich gaseous stream and a liquid recycle stream comprising one or more of these compounds (II) in the presence of a catalyst.

10 Claims, No Drawings

HYDROGENATION OF HALOGENATED COMPOUNDS

This application is a 371 of PCT/US95/14876, filed Nov. 15, 1995.

The present invention relates to a process for hydrogenating a halogenated compound which contains one or more >C=O, olefinic and/or aromatic >C=C< groups.

There is an increasing demand for methods of processing halogenated organic compounds which are for example comprised in fractionation column bottoms in the production of allyl chloride, ethylene dichloride or trichloroethylene, or in used dielectric fluids containing polychlorinated biphenyls and chlorinated benzene. Several methods exist of converting saturated halogenated organic compounds by hydrodehalogenation techniques to hydrogen halide and hydrocarbonaceous organic compounds having a decreased halogen content which may be safely and usefully employed or recycled. Such hydrodehalogenating techniques are for example described in U.S. Pat. Nos. 5,316,663 and 4,899,001.

However, it is known from U.S. Pat. No. 4,899,001 that unsaturated halogenated organic compounds present a greater challenge for subsequent processing, such as hydrodehalogenation, than the saturated halogenated organic compounds. For example, the presence of double bonds can interfere with the hydrodehalogenation reaction or polymerization may take place. Therefore, skilled artisans have searched for methods of converting unsaturated halogenated organic compounds to the corresponding saturated halogenated organic compounds.

U.S. Pat. No. 4,899,001 teaches a process wherein a) a first feedstock comprising unsaturated, halogenated organic compounds is reacted with hydrogen in a first hydrogenation reaction zone operated at mild hydrogenation conditions to produce a first hydrogenated stream comprising hydrocarbonaceous compounds, b) this first hydrogenated stream and a second feedstock comprising saturated, halogenated organic compounds are reacted with hydrogen in a second hydrogenation reaction zone operated at hydrogenation conditions selected to produce a stream comprising hydrocarbonaceous compounds and to generate at least one water-soluble inorganic halide compound. These two reaction steps are followed by several separation steps. The primary function of the hydrogenation reaction zone in step a) is the selective saturation of the unsaturated, halogenated compounds; however, dehalogenation, desulfurization, hydrocracking, may also take place.

Chemical Abstract No.116:255051 relates to studies on hydrogenation with nickel catalysts, particularly to catalytic properties of colloidal nickel for the hydrogenation of carbon—carbon double bonds.

Chemical Abstract No. 88:169335 relates to studies on hydrogenation of olefins catalyzed by polymer-bound palladium (II) complexes. It is disclosed that a polymer-bound $PdCl_2$ complex under mild conditions catalyzes the hydrogenation of alkenes and alkynes.

Chemical Abstract No. 85:176349 discloses an active palladium catalyst for the hydrogenation of organic compounds, such as 1-hexene, cyclohexene, PhCHO and $PhNO_2$, wherein Ph is phenyl.

However, hydrogenation of halogenated compounds which contain one or more >C=O, olefinic and/or aromatic >C=C< groups is an exothermic reaction. When the reaction is conducted on a large scale, the reaction temperature has to be carefully controlled.

GB-A-2,108,953 discloses a process for preparing 3-chloropropyl alcohol by hydrogenating 3-chloroallyl alcohol using palladium as a catalyst. The reaction is carried out in liquid phase, 3-chloroallyl alcohol is dissolved in a non-polar organic solvent, such as carbon tetrachloride, pentane, hexane, heptane, aromatic compounds, ketones or ethers. Preferred solvents are said to be cyclohexane and octane. By using such a solvent, the reaction temperature can be controlled, however, the solvent has to be separated from the product in an additional step after the reaction, which substantially increases the costs of the process.

Therefore, it would be desirable to provide a hydrogenation process which allows an efficient temperature control but which does not require subsequent separation of a solvent. It would be particularly desirable to provide a hydrogenation process which can be run continuously and, most preferably, which can be run on a large scale.

Accordingly, the present invention relates to a process for hydrogenating a halogenated compound (I) containing one or more >C=O, olefinic and/or aromatic >C=C< groups for producing a halogenated compound II having no or a decreased level of >C=O, olefinic and/or aromatic >C=C< groups. The process is characterized in that a liquid feed stream comprising one or more of said compounds (I) is contacted with a hydrogen-rich gaseous stream and a liquid recycle stream, comprising one or more of said compounds (II), in the presence of a catalyst.

Liquid feed streams which consist of one or more of the mentioned compounds (I) and liquid recycle streams which consist of one or more of the mentioned compounds (II) are also meant to be included in the terms "a liquid feed stream comprising one or more of said compounds (I)" and "a liquid recycle stream comprising one or more of said compounds (II)."

In the process of the present invention the reaction temperature can be efficiently controlled by conducting the hydrogenation in the presence of one or more compounds (II). Compound (II) is a reaction product resulting from the hydrogenation of compound (I). By "hydrogenation of compound (I)" is meant a partial or complete hydrogenation of the >C=O, olefinic and/or aromatic >C=C< groups in compound (I) without a substantial reduction of the halogen atoms by hydrodehalogenation and without substantial polymerization. The mentioned one or more compounds (II) may originate from various sources, however, at least a portion of compound(s) (II) originates from a liquid recycle stream which comprises one or more compounds (II). The liquid recycle stream comprising one or more compounds (II) serves as a reaction diluent which allows a continuous control of the reaction temperature. This way of controlling the temperature has considerable advantages over other methods. As described above, the reaction temperature can be controlled by adding an inert diluent, such as a hydrocarbon, to the reaction mixture. This method requires an additional separation step, as indicated above. Another method of temperature control would be the use of a jacketed reactor and a temperature control system for cooling the reactor. Again, this method of controlling the temperature would be very expensive. According to the present invention neither the presence of a hydrocarbon or a similar inert reaction diluent nor the use of a jacketed reactor and a sophisticated control system is necessary.

The halogenated compounds (I) may be brominated or fluorinated or, preferably, chlorinated. The halogenated compounds (I) may contain one or more halogen atoms. One or more types of halogen atoms may be present in the halogenated compounds (I). The halogenated compounds (I) preferably comprise from 2 to 24 carbon atoms, more preferably from 2 to 12 carbon atoms, most preferably from 2 to 6 carbon atoms.

The halogenated compounds (I) contain one or more >C=O, olefinic and/or aromatic >C=C< groups. The number of these groups is not limited. Olefinic carbon—carbon double bonds, if present, may be isolated or conjugated. Preferably, the total number of the >C=O, olefinic and/or aromatic >C=C< groups in the halogenated compounds (I) is from 1 to 12, more preferably from 1 to 6, most preferably from 1 to 4.

Additionally, the halogenated compounds (I) may contain one or more other heteroatoms, such as nitrogen, sulfur, oxygen and/or metal components. Furthermore, they may contain carbon-carbon triple bonds, carbon-nitrogen double bonds, carbon-nitrogen triple bonds, carbon-sulfur double bonds, carbon-phosphorus double bonds. Some or all of these double and triple bonds may be hydrogenated during the process of the present invention, depending on the amount of hydrogen and the type of catalyst. Depending on the type of catalyst used in the reaction of the present invention, the presence of such heteroatoms may be less desirable.

Exemplary of halogenated compounds (I) containing one or more >C=O groups are halogeno-alkyl alkyl ketones, such as chloromethyl methyl ketone or halogenated carboxylic acids, such as 2-chloro-2-propenoic acid.

Exemplary of halogenated compounds (I) containing one or more olefinic carbon—carbon double bonds are cis- or trans-1-chloro-1-propene, 2-chloro-1-propene, allyl chloride, cis- or trans-1,3-dichloro-1-propene, 2,3-dichloro-1-propene, 3,3-dichloro-1-propene, cis- or trans-1,4-dichloro-2-butene, hexachloro-1,4-butadiene and 2-chloro-3-propenol.

Exemplary of halogenated aromatic compounds (I) are 1-chloro-3-phenyl-1-propene, mono-, di-, tri-, tetra-, penta- or hexachlorobenzene and chlorophenols.

The halogenated aromatic compound (I) may contain one or more heteroatoms.

Preferred compounds (I) are olefinic or aromatic chlorinated compounds of 2 to 12 carbon atoms, more preferably olefinic chlorinated compounds of 2 to 6 carbon atoms or a mixture of two or more of such compounds, most preferably one or more chloropropenes.

Most preferably, the liquid feed stream used in the process of the present invention is at least partially a waste stream originating from the chemical production of various compounds, such as fractionating column bottoms in the production of allyl chloride, ethylene dichloride, trichloroethylene or perchloroethylene, or comprises recycled chemical compounds, such as used dielectric fluids containing polychlorinated biphenyls, chlorinated benzene or chlorinated solvents, and mixtures thereof.

The liquid feed stream containing one or more of the above-mentioned compounds (I) is contacted with a hydrogen-rich gaseous stream and a liquid recycled stream in the presence of a catalyst. The liquid feed stream may contain up to 100 percent, generally from 5 to 99 percent, preferably from 20 to 95 percent, and more preferably from 30 to 90 percent, of one or more of the above-mentioned compounds (I), based on the total weight of the liquid feed stream.

In addition to compound(s) I, the liquid feed stream may contain one or more non-halogenated saturated or unsaturated compounds such as, nitrites, ketones, aromatic compounds, alkenes or alkynes. Exemplary thereof are acetonitrile; acetone; $C_{2-6}$-alkenes, such as ethylene, propene, the butenes, hexenes, cyclohexene or the cyclohexadienes; $C_{2-6}$-alkynes, such as, propyne or the butynes; or benzene. Depending on the reaction conditions and on the catalyst used in the reaction, these compounds may also be hydrogenated. However, if present, the total weight of the non-halogenated saturated and unsaturated compounds generally is less than 50 percent, preferably less than 30 percent, more preferably less than 15 percent, based on the total weight of the liquid feed stream.

The liquid feed stream may also contain one or more halogenated saturated compounds, such as fluorinated or chlorinated saturated compounds which preferably comprise from 1 to 24, more preferably from 2 to 24, most preferably from 2 to 12 carbon atoms. Preferred compounds are chlorinated $C_{2-6}$-alkanes or chlorinated cycloalkanes, such as, monochloro, dichloro, trichloro or tetrachloro-ethanes, propanes, butanes, pentanes, hexanes, cyclopentanes or cyclohexanes. The most preferred halogenated saturated compounds are fully hydrogenated compounds I, that is, compounds (II). Alternatively, the liquid feed stream may contain one or more compounds (II) which have some, but a decreased level of, >C=O, olefinic and/or aromatic >C=C< group(s), as compared to the level of these groups in compound(s) (I). If present, the total amount of compound (s) (II) and/or one or more other halogenated saturated compounds in the liquid feed stream preferably is from 1 to 95 percent, more preferably from 5 to 80 percent, most preferably from 10 to 70 percent, based on the total weight of the liquid feed stream.

If the halogenated compound (I) comprises more than one >C=O, olefinic and/or aromatic >C=C< groups, some or all of these groups can be hydrogenated according to the present invention. Preferably, substantially all >C=O and >C=C< groups are hydrogenated, that means that preferably at least 90 percent, more preferably at least 95 percent and most preferably at least 98 percent of these groups are hydrogenated in the process of the present invention.

The molar ratio between the hydrogen in the hydrogen-rich gaseous stream and the total number of >C=O, olefinic and/or aromatic >C=C< groups in the halogenated compound(s) (I) preferably is at least 1:1, more preferably from 1:1 to 20:1, most preferably from 1:1 to 10:1. Besides hydrogen, the hydrogen-rich gaseous stream may comprise minor amounts of other components, such as $C_{1-6}$-alkanes or $C_{2-6}$-alkenes or hydrogen halide. Preferably, the weight of hydrogen amounts to at least 70 percent, preferably to at least 90 percent and more preferably to at least 98 percent. The amount of the other components preferably does not exceed 30 percent, more preferably 10 percent, most preferably 2 percent, based on the total weight of the hydrogen-rich stream.

The hydrogenation of the halogenated compound(s) (I) to the halogenated compound(s) (II) described below is conducted in the presence of a catalyst. Suitable hydrogenation catalysts are known in the art. Generally, they are based on one or more metals of Group VIII of the Periodic Table of Elements, such as iron, cobalt, nickel, ruthenium, rhodium, palladium, osmium, iridium or platinum, on carriers, such as activated carbon, silica, titanium dioxide, zirconium dioxide and/or alpha-, beta- or gamma-alumina. The hydrogenation catalyst may further contain one or more of the following components: alkali metals, alkaline earth metals, elements of group IIIa, IVa and Va and sulphur components.

The hydrogenation is generally conducted at a pressure of 1 to 100 bar, preferably 2 to 70 bar, more preferably 5 to 50 bar. The hydrogenation is preferably conducted at a temperature of up to 200° C., more preferably from 15° C. to 150° C., most preferably from 20° C. to 100° C. It may be desirable to heat the reactor(s) used for the hydrogenation or to preheat the liquid feed stream comprising compound(s)

(I) and/or the liquid recycle stream comprising compound(s) (II) at the beginning of the hydrogenation reaction if an initial elevated temperature is desired. However, when the exothermic reaction reaches its steady state, heating is stopped and the reactor(s) is/are preferably operated adiabatically. Preferred liquid residence times on the catalyst are from 0.5 to 60 minutes, more preferably from 1 to 25 minutes, most preferably from 2 to 15 minutes.

Advantageously, the ratio between the liquid recycle stream comprising one or more compounds (II) and the liquid feed stream comprising one or more compounds (I) is controlled such that the temperature in the hydrogenation reaction does not exceed 200° C. Preferably, the ratio between the two above-mentioned streams is controlled such that the temperature in the hydrogenation reaction is from 15° C. to 150° C., more preferably from 20° C. to 100° C. This ratio between the two streams can be controlled and regulated by keeping the flow of the liquid feed stream comprising compound(s) (I) constant and adjusting the flow of the liquid recycle stream comprising compound(s) (II) or vice versa. If the concentration of compound(s) (I) varies in the liquid feed stream, the liquid feed stream is preferably analyzed and its flow adjusted before it is fed into the hydrogenation reactor(s).

The weight ratio between compound(s) (II) and compound(s) (I) in the hydrogenation reaction is preferably from 1:1 to 100:1, more preferably from 2:1 to 50:1, most preferably from 5:1 to 40:1. It is to be understood that not the entire amount of compound(s) (II) must originate from the liquid recycle stream. A portion of compounds (II) present in the hydrogenation reaction may be comprised in the liquid feed stream, as described above. Furthermore, at the initial phase of the reaction, compound(s) (II) is/are preferably provided from another source as long as not a sufficient amount of compound(s) (II) is produced for providing a sufficient liquid recycle stream. When the reaction reaches a steady state, the only source of compound(s) (II) generally is the liquid recycle stream and optionally the liquid feed stream. In order to conduct a continuous and cost-efficient hydrogenation, it is essential that at least a portion of the compound(s) (II) comprised in the reaction mixture originates from the liquid recycle stream. Preferably from 20 to 100 percent, more preferably from 30 to 100 percent, most preferably from 50 to 100 percent of the total weight of compound(s) (II) comprised in the reaction mixture originates from the liquid recycle stream. It is to be understood that in the process of the present invention the liquid recycle stream may be subjected to one or more separation and/or purification steps before it is recycled to the hydrogenation reaction. For example compound(s) (II) may be separated from possible by-products and purified before feeding compound(s) (II) into one or more hydrogenation reactors. However, such separation and purification steps generally are not necessary and are not advantageous.

The hydrogenation reaction is generally conducted continuously in one or more reactors. Preferred reactor types are a heat-insulated drum without a jacket, an insulated tube or an insulated vessel which is internally equipped with multiple tubes. The use of jacketed vessels or heat exchangers, as reactors is not excluded, however, these reactors generally do not provide any special advantages. The liquid streams may flow co-currently or counter-currently to the hydrogen-rich gaseous stream. The liquid streams may flow from the bottom to the top or vice versa. The hydrogenation reactors may contain a fluidized, fixed or, preferably, a trickle catalyst bed. The reactor(s) may contain fillings which are inert under the conditions chosen in the reactor(s). Useful inert fillings are for example glass or ceramic beads.

The use of more than one reactor may be advantageous in case the liquid feed stream comprises a high concentration of compound(s) (I). If two or more reactors are used, preferably the entire amount of the liquid recycle stream comprising compound(s) (II) is fed into the first reactor and the liquid feed stream comprising compound(s) (I) is partially fed into the first reactor and partially into the subsequent reactor(s). The entire amount of the hydrogen-rich gaseous stream can be fed into the first reactor. Alternatively, the hydrogen-rich gaseous stream can be partially fed into the first reactor and partially into the subsequent reactor(s).

The reactor(s) is/are preferably kept at mild conditions which allow selective hydrogenation of the >C=O, olefinic and/or aromatic >C=C< groups in compounds (I) and at which the formation of undesired by-products by hydrodehalogenation or by polymerization is minimized. These conditions are described above in general and in the following examples in more detail.

It should be noted that the described reaction conditions are the preferred conditions when the hydrogenation reaction has reached a steady state. The produced compounds (II) have no or a decreased level of >C=O, olefinic and/or aromatic >C=C< groups. Generally, the molar ratio between the >C=O, olefinic and/or aromatic >C=C< groups in compounds (I) and the >C=O, olefinic and/or aromatic >C=C< groups in compounds (II) is at least 2:1, preferably at least 9:1, more preferably at least 19:1, and most preferably at least 49:1.

If the above-described liquid feed stream comprising one or more compounds (I) has been contacted with a molar excess of hydrogen as described above, the process of the present invention preferably comprises the following steps: a) contacting a liquid feed stream comprising one or more of the above-mentioned compounds (I) with the hydrogen-rich gaseous stream and a liquid recycle stream comprising one or more of the above-mentioned compounds (II) in the presence of a catalyst, b) separating the product stream obtained in step a) into a hydrogen-rich gaseous stream and a liquid product stream comprising one or more compounds (II) and c) recycling a portion of the liquid product stream comprising one or more compounds (II) to process step a).

The preferred reaction conditions in step a) are described above. The product stream obtained in step a) is preferably cooled before it is subjected to a gas/liquid separation in step b). The temperature in step b) preferably is from −10° C. to +50° C., more preferably from 5 to 30° C., most preferably from 10 to 25° C. The pressure in step b) generally is from 1 to 100 bar, preferably from 1 to 50 bar, more preferably from 1 to 6 bar. The pressure in step b) is preferably lower than the pressure in step a). Step b) can be conducted in a known gas/liquid separation device.

In step c) a portion of the liquid product stream comprising one or more halogenated compounds (II) is recycled to process step a). Preferably from 20 to 95 percent, more preferably from 25 to 90 percent of the total volume of the liquid product stream comprising one or more compounds (II) is recycled to step a). It may be advantageous to recycle a portion or all of the hydrogen-rich gaseous stream obtained in step b) to step a).

Compound(s) (II) obtained in the hydrogenation reaction can be further processed according to known methods, for example by hydrodehalogenation as described in U.S. Pat. Nos. 5,316,663 and 4,899,001.

The present invention is further illustrated by the following examples which should not be construed to limit the scope of the present invention. Unless stated otherwise, all ratios, parts and percentages are given by weight.

EXAMPLE 1

A vertically installed tube made of stainless steel was used as a hydrogenation reactor. The tube contained 100 g of a palladium catalyst on alumina. The remaining volume of the tube was filled with glass beads. The reactor was operated in a trickle-bed mode. The pressure in the hydrogenation reactor was controlled by means of a pressure control valve. The reactor effluent was cooled in a jacketed cooler, wherein the coolant has a temperature between 15° C. and 20° C. The effluent from the cooler was fed into a gas-liquid separator. Excess hydrogen and any hydrogen chloride and alkanes formed in the reaction as by-products leave the gas-liquid separator via a gas outlet at the top. The pressure in the gas-liquid separator was controlled by means of a pressure-control valve which was connected to the gas outlet of the gas-liquid separator. The liquid product stream was collected at the bottom of the gas-liquid separator. A portion of the liquid product stream was recycled to the hydrogenation reactor and the remainder was fed into a product vessel.

Before starting the hydrogenation process, hydrogen was fed into the hydrogenation reactor at a rate of 25 Nl/h. Liquid 1,2-dichloropropane was fed into the hydrogenation reactor at a rate of 300 g/h. The pressure in the hydrogenation reactor was adjusted to 41 bar. Feeding was continued until a sufficient liquid level was achieved in the gas-liquid separator. The pressure in the gas-liquid separator was adjusted to 6 bar. Thereafter, the liquid was recycled from the gas-liquid separator to the hydrogenation reactor at a rate of 600 g/h. Direct feeding of fresh 1,2-dichloropropane into the hydrogenation reactor was stopped. The temperature in the reactor was 20° C. A liquid feed stream consisting of 70 percent of 1,2-dichloropropane and 30 percent of 2,3-dichloropropene was introduced into the hydrogenation reactor at an initial rate of 30 g/h. The feed rate was gradually increased until the maximum temperature on the catalyst bed in the reactor had risen to 30° C. The final feed rate was 60 g/h. The liquid residence time on the catalyst bed was 6 minutes. As the hydrogenation reaction proceeded, the liquid level in the gas-liquid separator increased, but it was adjusted by means of a level-control valve which opened regularly to allow liquid to flow to the product vessel. Analysis of the liquid product by gas chromatography showed that the product consisted of 97 percent of 1,2-dichloropropane, 3 percent of hydrogen chloride and traces of propane. Analysis of the gas stream leaving the gas-liquid separator showed that it consisted of hydrogen and traces of hydrogen chloride and propane.

EXAMPLE 2

Example 1 was repeated, except that the liquid feed stream consisted of 70 percent of 1,2-dichloropropane, 20 percent of 1,3-dichloropropene and 10 percent of 3,3-dichloropropene. After the reaction had achieved a steady state, the liquid product consisted of 70 percent 1,2-dichloropropane, 19.5 percent of 1,3-dichloropropane, 8.5 percent of 1,1-dichloropropane, less than 1 percent of 1-chloropropane, less than 2 percent of hydrogen chloride and traces of propane. The gas stream leaving the gas-liquid separator consisted of hydrogen and traces of hydrogen chloride and propane.

EXAMPLE 3

Example 1 was repeated, except that the liquid feed stream consisted of 50 percent of 2-chloropropane, 10 percent of propene, 30 percent of 2-chloropropene, 8 percent of 1-chloropropene (sum of cis- and trans-isomers) and 2 percent of 3-chloropropene. The pressure in the gas-liquid separator was adjusted to 21 bar. After the reaction had achieved a steady state, the liquid product consisted of 80 percent of 2-chloropropane, 10 percent of 1-chloropropane, 8 percent of propane and 2 percent of hydrogen chloride. The gas stream leaving the gas-liquid separator contained about 1 percent of propane, the rest being hydrogen. No hydrogen chloride was found.

I claim:

1. A process for hydrogenating a chlorinated alkene containing one olefinic >C=C< group and 2 to 12 carbon atoms for producing a chlorinated alkane, wherein a liquid feed stream comprising a chlorinated alkene is contacted with a hydrogen-rich gaseous stream and a liquid recycle stream, comprising a chlorinated alkane in the presence of a catalyst, and the ratio between the liquid recycle stream and the liquid feed stream is controlled such that the temperature during the hydrogenation is from 15 to 150° C.

2. The process of claim 1, wherein the ratio between the liquid recycle stream and the liquid feed stream is controlled such that the temperature during the hydrogenation is from 20 to 100° C.

3. The process of claim 1 or claim 2, wherein the pressure during the hydrogenation is from 2 to 70 bar.

4. The process of claim 1, wherein the hydrogenation is conducted in the presence of a molar excess of hydrogen and the process comprises the steps of
   a) contacting a liquid feed stream comprising a chlorinated alkene with a hydrogen-rich gaseous stream and a liquid recycle stream comprising a chlorinated alkane in the presence of a catalyst,
   b) separating the product stream obtained in step a) into a hydrogen-rich gaseous stream and a liquid product stream comprising the chlorinated alkane and
   c) recycling a portion of the liquid product stream comprising the chlorinated alkane to step a).

5. The process of claim 1, wherein the weight ratio between the chlorinated alkane(s) and the chlorinated alkene (s) in the hydrogenation reaction is from 1:1 to 100:1.

6. The process of claim 5, wherein the weight ratio between the chlorinated alkane(s) and compound(s) (I) the chlorinated alkene(s) in the hydrogenation reaction is from 5:1 to 100:1.

7. The process of claim 4, wherein the temperature in step b) is from −10 to +50° C.

8. The process of one of claims 1 or 4, wherein the chlorinated alkene is a chlorinated alkene of 2 to 6 carbon atoms or a mixture of two or more such compounds.

9. The process of claim 8, wherein the chlorinated alkene is chloropropene(s).

10. The process of claim 9; wherein the liquid feed stream is at least partially a stream originating from the fractionating column bottoms in the production of allyl chloride or ethylene chloride.

* * * * *

UNITED STATES PATENT AND TRADEMARK OFFICE
CERTIFICATE OF CORRECTION

PATENT NO. : 5,914,432

DATED : 6/22/99

INVENTOR(S) : LUME - PEREIRA

It is certified that error appears in the above-identified patent and that said Letters Patent is hereby corrected as shown below:

Column 8, line 57, delete "claim 9" and insert --claim 8--.

Signed and Sealed this

Nineteenth Day of October, 1999

Attest:

Q. TODD DICKINSON

Attesting Officer

Acting Commissioner of Patents and Trademarks